(12) United States Patent
Madhavi et al.

(10) Patent No.: US 7,446,101 B1
(45) Date of Patent: Nov. 4, 2008

(54) BIOAVAILABLE CAROTENOID-CYCLODEXTRIN FORMULATIONS FOR SOFT-GELS AND OTHER ENCAPSULATION SYSTEMS

(75) Inventors: Doddabele L. Madhavi, Worcester, MA (US); Daniel I. Kagan, Belmont, MA (US)

(73) Assignee: Bioactives, LLC, Belmont, MA (US)

( * ) Notice: Subject to any disclaimer, the term of this patent is extended or adjusted under 35 U.S.C. 154(b) by 0 days.

(21) Appl. No.: 10/735,335

(22) Filed: Dec. 12, 2003

(51) Int. Cl.
*A61K 31/047* (2006.01)
*A61K 31/724* (2006.01)

(52) U.S. Cl. ........................ 514/58; 514/738

(58) Field of Classification Search .......... 435/166, 435/67; 514/58, 975, 762; 536/46; 34/284; 424/725, 451, 456; 568/824, 825
See application file for complete search history.

(56) References Cited

U.S. PATENT DOCUMENTS

| | | | | |
|---|---|---|---|---|
| 4,125,630 | A * | 11/1978 | Orthoefer | 426/104 |
| 4,929,774 | A * | 5/1990 | Fukamachi et al. | 568/824 |
| 5,221,735 | A * | 6/1993 | Leuenberger et al. | 536/4.1 |
| 5,384,186 | A | 1/1995 | Trinh et al. | |
| 6,313,169 | B1 | 11/2001 | Bowen et al. | |
| 6,569,463 | B2 * | 5/2003 | Patel et al. | 424/497 |
| 2004/0109920 | A1 * | 6/2004 | Reuscher et al. | 426/73 |

OTHER PUBLICATIONS

Szente, L. et al "Stabilization and stabilization of lipophilic natural colorants with cyclodextrins" J. Incl. Phen. (1998) vol. 32, pp. 81-89.*
Basu, H. et al "Encapsulated carotenoid preparations . . . " JAOCS (2001) vol. 78, No. 4, pp. 375-380.*
Hedges, A. "Industrial applications of cyclodextrins" (1998) vol. 98, pp. 2035-2044.*
Olmedill, B. "A European multicentre, placebo-controlled supplementation . . . " Clin. Sci. (2002) vol. 102, pp. 447-456.*
Pfitzner, I. et al "Carotenoid: methyl-beta-cyclodextrin formulations . . . " BBA (2000) vol. 1474, pp. 163-168.*
Kulevskaya, V. et al "Stability of beta-carotene in complexes . . . " Pharm. Chem. J. (2002) vol. 36, No. 1, pp. 36-39.*
Sharper, P. "When bioavailability or stability is a problem" http://www.samedanltd.com/members/archives/PMPS/Autumn2001/PeterSharper.htm, retrieved Mar. 30, 2006.*
Mele, A. et al "Non-covalent associations of cyclomaltooligosaccharides (cyclodextrins) with carotenoids in water" Carbohyd. Res. (2002) vol. 337, pp. 1129-1136.*

Yu, et al., "Effect of camphor/cyclodextrin complexation on the statility of O/W/O multiple emulsions", Int J Pharm Aug. 11, 2003;261(1-2);1-8.
Valero, et al., "Ternary naproxen: beta-cyclodextrin:polyethylene glycol complex formation", Int J Pharm Oct. 20, 2003; 265(1-2):141-9.
Tonnesen, et al., "Studies of curcumin and curcuminoids, XXVII. Cyclodextrin complexation: solubility, chemical and photochemical stability", Int J Pharm. Sep. 5, 2002;244(1-2).
Mura, et al., "Influence of the Preparation Method on the Physicochemical Properties of Binary Systems of Econazole with Cyclodextrins", Int Journ of Pharm 193 (1999) 85-95.
Lockwood, et al., "Improved Aqueous Solubility of Crystalline Astaxanthin (3,3'-dihydroxy-B,B-carotene-4,4"-dione) by Captisol (Sulfobutyl Ether B-Cyclodextrin)", Jour of Pharm Sci, vol. 92, 922-926 (2003).
Miyake, et al., "Improvement of solubility and oral bioavailability of rutin complexation with 2-hydroxypropyl-beta-cyclodextrin", Pharm Dev technol 2000;5(3) :399-407.
Baskaran, V., Sugawara, T., and Nagao, A., Phospholipids affect the intestinal absorption of carotenoids in mice, Lipids, 2003, 38: 705-11.
Xie W., Xu, W., and Feng, G., Study on the inclusion interaction of beta-cyclodextrin with phosphatidylcholine by UV spectra, Guang Pu Xue Yu Guang Pu Fen Xi, 2001 21(5): 707-9. (Article in Chinese)1, abstract only.
Anderson, T.G., Tan, A., Ganz, P., and Seelig, J., Calorimetric measurement of phospholipids interaction with methyl-beta-cyclodextrin, Biochemistry, 2004, 43: 2251-2261.
Bowen, P.E., Herbst-Espinosa, S. M., Hussain, E.A., and Stacewicz-Sapuntzakis, M., Esterification does not impair lutein bioavailability in humans, J Nutr. 2002, 132(12): 3668-3673.

* cited by examiner

*Primary Examiner*—Leigh C Maier
(74) *Attorney, Agent, or Firm*—Mueller Smith

(57) ABSTRACT

The present invention describes an improved commercial process for the production of carotenoid-cyclodextrin complexes and formulation of the complex for human ingestion. Complexation with cyclodextrins (e.g., α-cyclodextrin, β-cyclodextrin, γ-cyclodextrin, or HP-β-cyclodextrin) significantly improves the uptake of carotenoids (e.g., lycopene, lutein, or zeaxanthin) and their mixtures in vitro. The method for making such complexes includes forming a carotenoid/cyclodextrin complex; freezing drying said carotenoid/cyclodextrin complex; and blending said freeze-dried carotenoid/cyclodextrin complex with a mixture of lecithin and a vegetable oil or a vegetable oil suitable for soft gelatin capsules. The cyclodextrin/carotenoid complex can be formed in a molar ratio of between about 0.5:1.0 and 10:1. In vivo, in a human study, the lutein/γ-cyclodextrin complex formulated in lecithin-oil or oil showed a better absorption of lutein, as compared to the free lutein-oil formulation.

3 Claims, 4 Drawing Sheets

BIOAVAILABLE CAROTENOID-CYCLODEXTRIN FORMULATIONS FOR SOFT-GELS AND OTHER ENCAPSULATION SYSTEMS

CROSS-REFERENCE TO RELATED APPLICATIONS

None

STATEMENT REGARDING FEDERALLY SPONSORED RESEARCH

Not applicable.

FIELD OF THE INVENTION

The invention generally relates to the development of a more bioavailable form of carotenoid-cyclodextrin complexes and formulations suitable for administration to humans in a variety of forms, including, for example, as soft gelatin capsules.

BACKGROUND OF THE INVENTION

Dietary carotenoids provide health benefits by reducing the risk of several chronic disorders. Some of the carotenoids found in the human serum and organs include, for example, β-carotene, lycopene, lutein, and zeaxanthin. The provitamin A activity of β-carotene is well documented. All trans-lutein and all trans-zeaxanthin are the predominant carotenoids found in the human macular pigment. Recent studies have demonstrated a direct relationship between the macular pigment density and age related macular degeneration. Epidemiological and experimental studies have indicated that these carotenoids may prevent age related macular degeneration and other blinding disorders. Lycopene, one of the major carotenoids in the human serum and organs, is reported to reduce the risk of certain types of cancers, such as prostate cancer, digestive tract cancers, and lung cancer. Lycopene also has been reported to be protective against cardiovascular diseases.

Consequently, many dietary supplements, containing isolated carotenoids in their free or esterified forms or mixtures of carotenoids in oil dispersions or as microencapsulated beadlets, now are commercially available. Being lipophilic molecules insoluble in water, the absorption of carotenoids depends on a variety of factors such as, for example, dietary fats, digestive process, and extent of micellarization.

In human studies, both free and esterified forms of lutein showed large variations in absorption (Bowen, P. E., Herbst-Espinosa, S. M., Hussain, E. A., and Stacewicz-Sapuntzakis, M., "Esterification does not impair lutein bioavailability in humans", *J. Nutr.*, 132: 3668-3673, 2002). Zeaxanthin, the stereoisomer of lutein, was less well absorbed than an equal lutein dose in a human study (Bone, R. A., Landrum, J. T., Guerrs, L. H., and Ruiz, C. A., "Lutein and zeaxanthin supplements raise macular pigment density and serum concentrations in humans", *J. Nutr.*, 133: 992-998, 2003). High interindividual variability in lycopene absorption has been reported in human studies (Diwadkar-Navsariwala, V., Novotny, J. A., Gustin, D. M., Sosman, J. A., Rodvold, K. A., Crowell, J. A., Stacewicz-Sapuntzakis, and M., Bowen, P. E., "A physiological pharmacokinetic model describing the disposition of lycopene in healthy men", *J. Lipid Res.*, 44: 1927-1939, 2003). Improving the uptake of carotenoids, thus, is of interest to the nutritional supplement and pharmaceutical industry.

Cyclodextrins are cyclic oligosaccharides composed of 6, 7, or 8 α-(1-4)-linked anhydroglucose units with a hydrophobic cavity suitable for inclusion of various lipophilic compounds. The α-, β-, and γ-cyclodextrins prepared from starch are considered natural and are GRAS according to the USFDA. Various substituted derivatives, such as, for example, methyl- and hydroxypropyl-cyclodextrins also have been developed to improve the solubility and complexation properties of cyclodextrins. The cyclodextrins are widely used in the pharmaceutical industry to improve the dissolution, sustained release, and uptake of lipophilic compounds.

It is well known in the art that complexation with different cyclodextrins results in products with varying properties. For example, dimethyl β-cyclodextrin was reported to dramatically enhance the absorption of insulin, while hydroxypropyl β-cyclodextrin had no significant effect (Shao, Z., Li, Y., Chermak, T., and Mitra, A. K, "Cyclodextrins as mucosal absorption promoters of insulin. II. Effects of beta-cyclodextrin derivatives on alpha-chymotryptic degradation and enteral absorption of insulin in rats", *Pharm Res.*, 11:1174-1179, 1994).

The differences in the cavity size of cyclodextrins (α-<β-<γ-) provide some selectivity for complexation with guest molecules. Small molecules with four or fewer carbon atoms form better complexes with α-cyclodextrin, while larger molecules bind best with γ-cyclodextrin. Based on the solubility profile of the natural cyclodextrins, complexes with β-cyclodextrin generally are less soluble as compared to the γ-cyclodextrin complexes. Cyclodextrins also may exhibit stereoselectivity with a mixture of enantiomers resulting in differences in the stability of the complexes formed between each enantiomer and the cyclodextrin and differences in the rate of dissolution and release properties from the complexes.

It is also known in the art that the excipients used in formulations, such as, for example, surfactants, oils, waxes, and phospholipids, may interact with cyclodextrin. This interaction may result in the dissociation of the complex, inhibit the release of the actives (e.g., active ingredients or components), or modulate the dissolution properties (Veiga, M. D. and Ahsan, F., "Influence of surfactants (present in the dissolution media) on the release behavior of tolbutamide from its inclusion complex with beta-cyclodextrin", Eur. *J. Pharm. Sci.*, 9: 291-299, 2000; Ahsan, F., Arnold, J. J., Meezan, E., and Pillioin, D. J., "Mutual inhibition of insulin absorption-enhancing properties of dodecylmaltoside and dimethyl-beta-cyclodextrin following nasal administration", *Pharm. Res.*, 18; 608-614, 2001; Shalko-Basnet, N., Pavelic, Z., and Becirevic-Lacan, M., "Liposomes containing drug and cyclodextrin prepared by the one-step spray-drying method", *Drug Dev. Ind. Pharm.*, 26: 1279-84, 2000).

Complexation of carotenoids, such as, for example, β-carotene and lycopene, with α- and β-cyclodextrins, for example, has been tried by a few investigators as a means to improve their dissolution properties and stability to light and heat (U.S. Pat. Nos. 5,834,445 and 5,221,735). The complexed products are targeted for functional foods and beverages, or for topical applications.

U.S. patent application Ser. No. 10/309,999 describes a process for complexation of lutein with γ-cyclodextrin followed by spray drying as the preferred method of drying. The application has certain drawbacks. Since lutein is not fully protected by complexation, the process may result in reduced product recovery and loss of lutein concentration as a result of exposure to temperature and humidity during the drying and collection of finished product. The application does not explore complexation of lutein with other cyclodextrins or of other carotenoids with cyclodextrins. The application also does not address formulation of the lutein-cyclodextrin complex for incorporation into soft gelatin capsules or other suitable methods of delivery.

BRIEF SUMMARY OF THE INVENTION

The present invention describes an improved commercial process for the production of carotenoid-cyclodextrin complexes and formulation of the complex for human ingestion. The carotenoids selected include, inter alia, lutein, lycopene, and a mixture of lutein:zeaxanthin. The cyclodextrins selected from among natural cyclodextrins and their derivatives such as, for example, α-, β-, γ-cyclodextrin, and HP-β-cyclodextrin.

The present invention is based on the unexpected discovery that the commercial method of drying and formulation impacts the ability to retain the high bioavailability of lutein from a lutein-cyclodextrin complex. One of the inventive bioavailable forms is a freeze-dried lutein/γ-cyclodextrin complex formulated in lecithin-vegetable oil or vegetable oil for soft gelatin capsules to be used in the nutritional supplement and pharmaceutical industry. The inventive freeze-dried complex shows a highly significant uptake in vitro in Caco2 intestinal cells as compared to, for example, a spray-dried complex described in U.S. patent application Ser. No. 10/309,999. The complex on formulation shows a significant uptake in vitro in the same model based on the excipients used in formulation.

The present invention also is based on the unexpected discovery that the process can be adapted with modifications to other carotenoids, including, inter alia, lycopene and mixtures of carotenoids, such as, for example, lutein and zeaxanthin, and to other cyclodextrins such as, for example, α-, β-, γ-, and hydroxypropyl β-cyclodextrins (HP-β).

The present invention also is based on the unexpected discovery that the in vitro uptake of lutein and zeaxanthin from the α-cyclodextrin complex is comparable to the γ-cyclodextrin complex neat.

The invention also discloses simultaneous uptake of stereoisomers lutein and zeaxanthin from cyclodextrin complexes.

The present invention, then, is a method for making a bioavailable carotenoid-cyclodextrin complex for animal ingestion. This method includes commercial production of the complex and formulating the complex for soft gelatin capsules to retain the properties of the complex. The preferred animal is a human with the route of administration being oral ingestion. The form of the complex for ingestion is a soft gelatin capsule, which may contain other ingredients, both active and inactive. In vivo, in a human study, the lutein/γ-cyclodextrin complex improved the absorption of lutein as compared to a commercially available free lutein-oil formulation.

BRIEF DESCRIPTION OF THE DRAWINGS

For a fuller understanding of the nature and advantages of the present invention, reference should be had to the following detailed description taken in connection with the accompanying drawings, in which.

Figure 1:
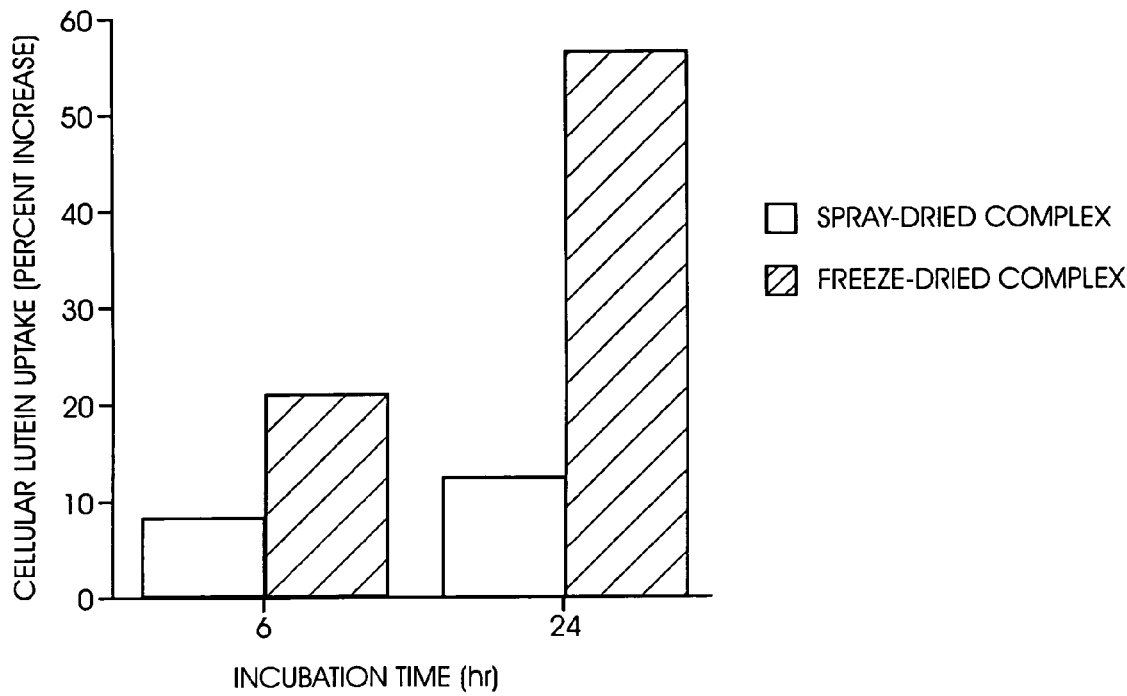
FIG. 1 represents the effects of drying of the lutein/γ-cyclodextrin complex on the uptake of lutein by Caco2 cells as reported in Example 1.

The drawings will be described further in connection with the Examples set forth below.

DETAILED DESCRIPTION OF THE INVENTION

The present invention discloses the commercial production of highly bioavailable forms of carotenoids with cyclodextrins, and soft gelatin formulations for use in the nutritional supplement and the pharmaceutical industry. The α-, β-, γ-, and HP-β-cyclodextrins were obtained from commercial sources. The carotenoids used were all trans-lutein, all trans-lycopene and a mixture of all trans-lutein:zeaxanthin (1:1.6).

Commercially available crystalline all trans-lutein (manufactured under U.S. Pat. No. 6,380,442) was used for complexation. The molar ratio of cyclodextrin to lutein can range, for example, from about 0.5:1 to 10:1, and preferably from about 1:1 or 2:1 for commercial production. The lutein concentration in the complex can range, for example, from about 0.1 to 30% (w/w). The lutein/γ-cyclodextrin complex (1:2 molar) was prepared based on methods known in the art in an aqueous slurry at room temperature using homogenization for about 1-3 hours. The mixture was kept under refrigeration overnight before drying. The slurry was dried by freeze-drying using a commercial tray, freeze dryer (Virtis). The product (40 kg) was an orange powder containing 20% lutein with a 95% recovery of the product, as compared to a 50% loss with spray-drying the complex.

The lutein was complexed with α-, β-, and HP-β-cyclodextrins using modified techniques based on the cyclodextrins and complexation efficiency, and the complexes were freeze dried. The modifications included, kneading the two components in the presence of a small volume of organic solvent, such as, for example, acetone or ethanol (~0.1% w/w of the components) before aqueous homogenization; or addition of solvents during aqueous slurry homogenization; or addition of polymers such as, for example, carboxymethyl cellulose (~0.1-0.2%) to solubilize one of the components to facilitate complexation.

Based on the results, crystalline all trans-lycopene (isolated under U.S. Pat. No. 6,380,442) and the all trans-lutein/zeaxanthin mixture (prepared by isomerization of lutein) also were complexed with α-, β-, γ-, and HP-β-cyclodextrins followed by freeze drying.

The uptake of carotenoids from the inclusion complexes was determined using an in vitro Caco2 intestinal cell culture model. This cell line has been used as a model system to examine the selective characteristics of intestinal absorption of compounds, including, interalia, carotenoids (Garrett, D. A., Fulla, M. L., Sarama, R. J., and Craft, N., "Accumulation and retention of micellar β-carotene and lutein by Caco2 human intestinal cells", *J. Nutr. Biochem.*, 10: 573-581, 1999); vitamin E (Traber, M. G., Goldberg, I., Davidson, E., Lagamy, N., and Kayden, H. J., "Vitamin E uptake by human intestinal cells during lipolysis in vitro", *Gastroenterology*, 98: 96-103, 1990); retinol, beta-lactoglobulin, palmitic acid (Puyol, P., Perez, M. D., Sanchez, L., Ena, J. M., and Calco, M., "Uptake and passage of beta lactoglobulin, palmitic acid and retinal across the Caco2 monolayer", *Biochim. Biophys. Acta.*, 1236: 149-154, 1995); and polyamines (Turchanowa, M. V., Stein, L., and Caspary, W. F., "Transepithelial transport of putrescine across monolayers of the human intestinal epithelial cell line, Caco2", *World J. Gastroenterol.*, 7: 193-197, 2001). The cells spontaneously differentiate at confluency into cells that exhibit phenotypic properties that are similar to those of mature enterocytes, including a highly differentiated brush border.

The in vitro model also has been used to determine the effects of formulation on the uptake of the actives. A recent study has indicated that polyethylene glycol, Tween 80, PEG 400, HP-β-cyclodextrin do not affect the viability of the 21 day cultured cells and that testing these formulations on the cells can predict intestinal absorption of poorly water soluble drugs in humans (Takahashi, Y., Kondo, H., Yasuda, T., Watanabe, T., Kobayashi, S., and Yokohama, S., "Common solubilizers to estimate the Caco2 transport of poorly water-soluble drugs", *Int. J. Pharm.*, 246: 85-94, 2002).

The results of the in vitro study conducted during work on the present invention showed a highly significant uptake from the freeze-dried lutein/γ-cyclodextrin complex as compared to the spray-dried product. Such discovery forms one basis of the present invention.

The in vitro study also showed significant uptake from the α-, β-, γ-, and HP-β-complexes as compared to the lutein in mixed micelles or in liposomes. It was of interest to note that the α-cyclodextrin complex showed comparable uptake to the γ-cyclodextrin complex.

A significant improvement in the uptake also was observed with the lycopene-cyclodextrin and lutein/zeaxanthin-cyclodextrin complexes in vitro. With the lutein/zeaxanthin mixture, HPLC analysis of the cellular carotenoids indicated the uptake of both the compounds from the inclusion complexes and the ratio of cellular lutein to zeaxanthin was 1:1.6.

Since the carotenoids are not completely protected from degradation by the complexation, further formulations are necessary for incorporation into the soft gelatin capsules. The lutein/γ-cyclodextrin complex was used as an example. Formulation of the complex was surprisingly found to be a highly critical factor in retaining the properties of the complex. The complex was dispersed in different excipients used in soft-gel formulations, such as, for example, vegetable oils, medium chain triglycerides, synthetic surfactants (such as polysorbate 80), lecithin, and combinations thereof. These components are known to protect lutein from degradation. The uptake of lutein from these formulations was tested using the Caco2 cell culture model. It was found unexpectedly that, of all the formulations tested, the lecithin-oil formulation resulted in a high uptake of lutein from the complex. Suitable such vegetable oils are edible and can be one or more, for example, of cocoanut oil, corn oil, cottonseed oil, oat oil, olive oil, palm oil, palm kernel oil, peanut oil, rapeseed oil, rice bran oil, safflower oil, sesame seed oil, soybean oil, or sunflower oil. The weight ratio of lecithin to vegetable oil can range from between about 10:1 and 1:1.

Based on these results, the lutein/γ-cyclodextrin complex was used as an example to study the in vivo absorption in human studies. The lecithin-oil and oil formulations were tested in a human study in soft gelatin capsules containing 20 ng lutein/capsule versus commercially available lutein-oil soft gelatin capsules. The results indicated that the lutein-cyclodextrin complex showed a better absorption, as compared to the free lutein-oil formulation, in eight of the nine subjects. Interestingly the study also indicated that those subjects with the lowest lutein uptake had the greatest gain with the lutein-cyclodextrin. The cyclodextrin complex significantly aided subjects with difficulties in lutein absorption from the oil formulation.

While the invention has been described with reference to a preferred embodiment, those skilled in the art will understand that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. In this application all units are in the metric system and all amounts and percentages are by weight, unless otherwise expressly indicated. Also, all citations referred herein are expressly incorporated herein by reference.

EXAMPLES

Example 1

Uptake of Lutein from Lutein-/γ-Cyclodextrin Complex Dried by Different Methods In Vitro Freeze-dried and spray-dried inclusion complexes containing 20%-21% lutein were used for the studies. The samples were dispersed in phosphate buffered saline (PBS) using sonication.

Cellular Uptake

Caco2 (ATCC, Rockville, Md.) cells were maintained in high glucose DMEM with 15 mM HEPES and 10% heat inactivated fetal bovine serum, nonessential amino acids, glutamine, and pyruvate in a humidified atmosphere at 5% $CO_2$ and 37° C. The cells were allowed to reach confluency (5-6 days after subculture) and differentiate (14 days) before commencement of the experiment. The test samples were diluted in the culture medium for the experiment. The monolayers were washed with PBS before adding the test samples at known lutein concentration. The cultures were incubated as before for 6 and 24 hours. At indicated times, the medium was removed, the monolayers were washed with PBS, followed by three washes with 5 mM sodium taurocholate in PBS. The bile salt wash removes the lutein adhering to cell surfaces. The cells were scraped into cold PBS and pelleted using centrifugation. The lutein was extracted using cold methanol and diethyl ether after a freeze-thaw cycle. The lutein content was estimated by spectrophotometry and HPLC.

The concentration of the test samples used was not cytotoxic to the cells, as determined by the gross morphological appearance of the monolayers, and the total protein content per flask was similar in cultures incubated with and without the test samples. One set of flasks from each treatment was used to determine the protein content.

Observations

The results recorded are displayed below and in FIG. 1.

TABLE 1

Effect of Drying on the Uptake of Lutein from the
Lutein/γ-Cyclodextrin Complex by Caco2 Cells

| Sample | Cellular Lutein Uptake (Percent Increase) | |
|---|---|---|
| | 6-hr Incubation | 24-hr incubation |
| Spray-dried Lutein/γ-cyclodextrin Complex | 8.75 | 14.35 |
| Freeze-dried Lutein/γ-cyclodextrin Complex | 20.5 | 56.1 |

The above-tabulated results indicate that the lutein uptake from the freeze-dried γ-cyclodextrin complex was much higher as compared to the spray-dried complex.

Example 2

Uptake of Lutein from Various Cyclodextrin Complexes In Vitro

The in vitro uptake of lutein from the cyclodextrin complexes was tested using the protocol detailed in Example 1. As a comparison, lutein incorporated into liposomes and mixed micelles was tested. The lutein-liposome stock solution was prepared using phosphatidylcholine and free lutein in PBS. The components were dissolved in dichloromethane, mixed at specified concentrations (5% lutein:95% phosphatidylcholine) and the solvent was evaporated using $N_2$. The residue was sonicated in PBS to obtain the liposomes. Mixed micelles were prepared using sodium taurocholate (bile salt), monoacylglycerol, oleic acid, phosphatidylcholine, lysophosphatidylcholine, and lutein in PBS. The components were dissolved in dichloromethane except for the taurocholate, and mixed at specific concentrations. The solvent was evaporated to dryness. The taurocholate was added as an aqueous solution, followed by the addition of PBS, sonication, and filtration to obtain a micellar dispersion of lutein.

Observations

Figure 2:
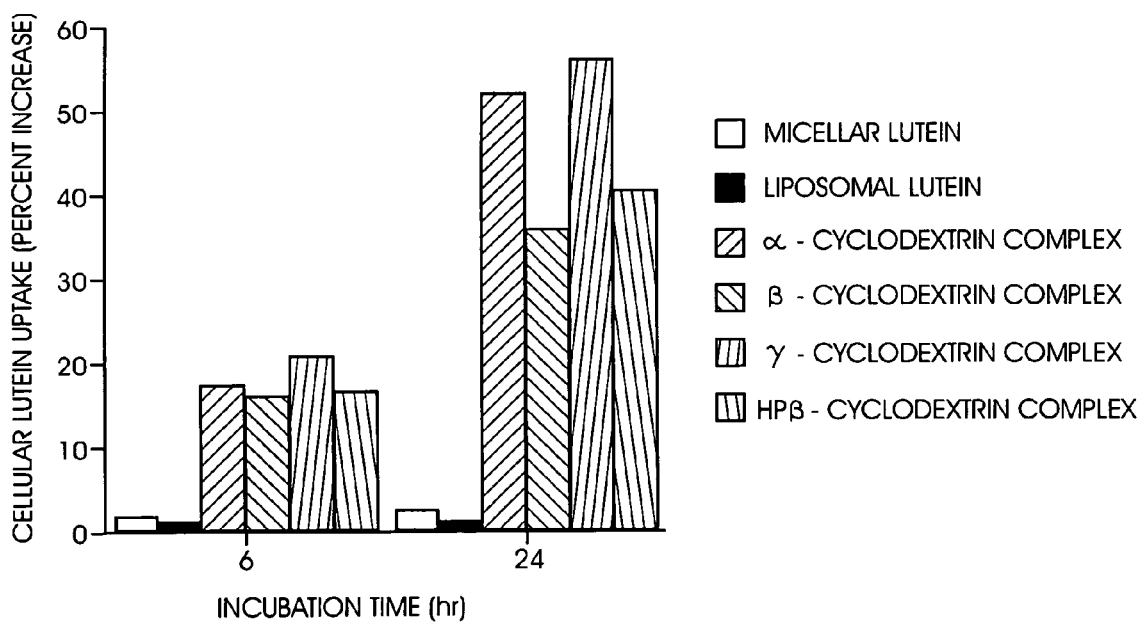
FIG. 2 represents a comparison of uptake of lutein from cyclodextrin complexes by Caco2 cells as reported in Example 2.

The results recorded are displayed below and presented in FIG. 2. The highest uptake was observed with the γ-cyclodextrin complex, followed closely by the α-cyclodextrin complex. Complexation in general significantly improved the uptake as compared to the micellar and liposomal preparations.

TABLE 2

A Comparison of the Uptake of Lutein from Cyclodextrin
Complexes by Caco2 Cells

| Sample | Cellular Lutein Uptake (Percent Increase) | |
|---|---|---|
| | 6-hr Incubation | 24-hr incubation |
| Micellar Lutein | 1.4 | 2.16 |
| Liposomal Lutein | 0.86 | 0.86 |
| Lutein/α-Cyclodextrin Complex | 17.0 | 51.8 |
| Lutein/β-Cyclodextrin Complex | 15.6 | 35.8 |
| Lutein/γ-Cyclodextrin Complex | 20.5 | 56.1 |
| Lutein/HP-β-Cyclodextrin Complex | 16.1 | 40.3 |

Example 3

Uptake of Lycopene from Various Cyclodextrin Complexes In Vitro

The in vitro uptake of lycopene from the cyclodextrin complexes and a liposomal preparation was tested using the protocol detailed in Example 1. The liposomal lycopene was prepared as described in Example 2.

Observations

Figure 3:
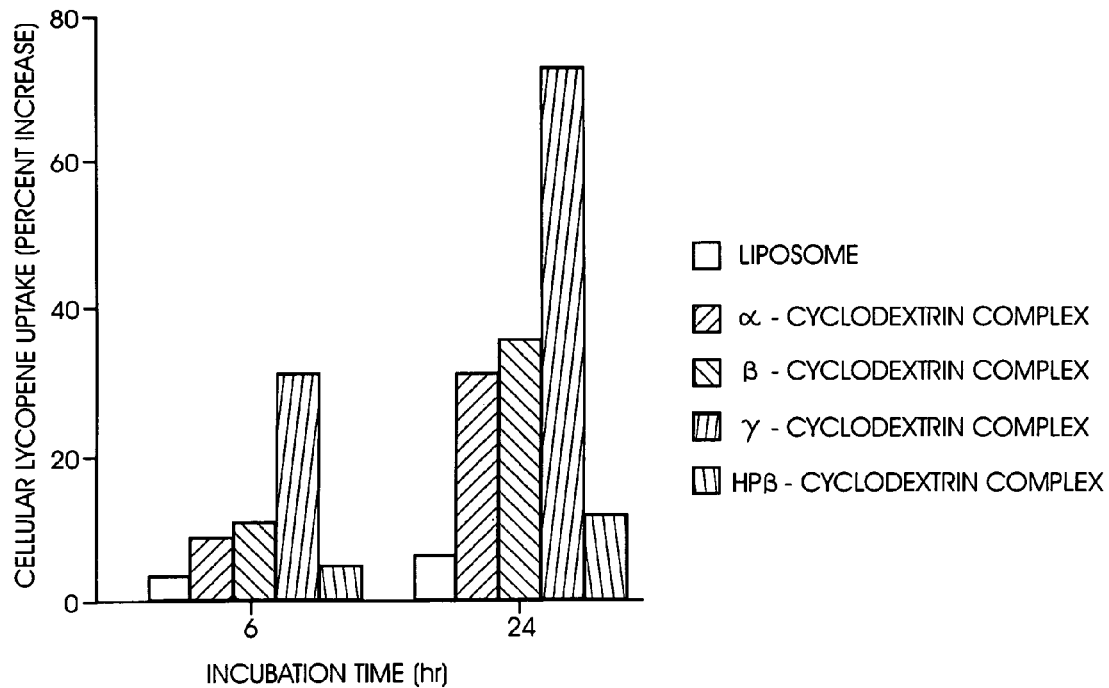
FIG. 3 represents a comparison of uptake of lycopene from cyclodextrin complexes by Caco2 cells as reported in Example 3.

The results recorded are displayed below and presented in FIG. 3. Cyclodextrin complexation in general improved the uptake as compared to the liposomal preparation. Of the cyclodextrin complexes tested, the highest uptake was observed with the γ-cyclodextrin complex.

TABLE 3

A Comparison of the Uptake of Lycopene from Cyclodextrin
Complexes by Caco2 Cells

| Sample | Cellular Lutein Uptake (Percent Increase) | |
|---|---|---|
| | 6-hr Incubation | 24-hr incubation |
| Lycopene Liposome | 3.5 | 6.3 |
| Lycopene/α-Cyclodextrin Complex | 8.8 | 30.9 |
| Lycopene/β-Cyclodextrin Complex | 10.6 | 27.1 |
| Lycopene/γ-Cyclodextrin Complex | 31.0 | 72.1 |
| Lycopene/HP-β-Cyclodextrin Complex | 5.0 | 11.65 |

Example 4

Uptake of Lutein and Zeaxanthin from Various Cyclodextrin Complexes In Vitro

The in vitro uptake of lutein and zeaxanthin from the cyclodextrin complexes was tested using the protocol detailed in Example 1.

Observations

Figure 4:
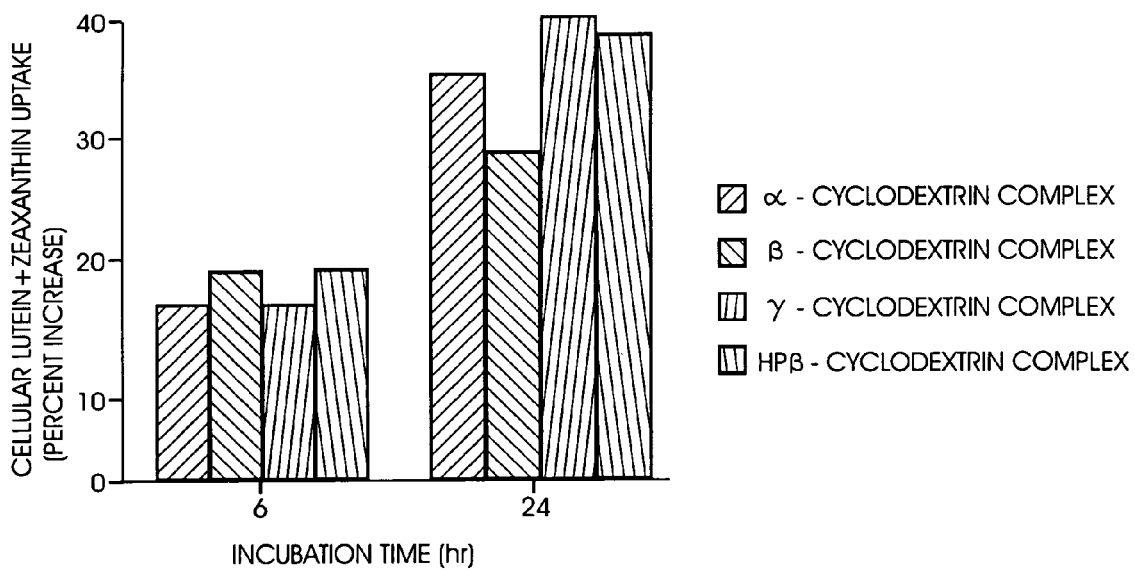
FIG. 4 represents a comparison of uptake of lutein and zeaxanthin from cyclodextrin complexes by Caco2 cells as reported in Example 4.

The results recorded are displayed below and presented in FIG. 4. Of the cyclodextrin complexes tested, the α-, HP-β- and γ-complexes showed comparable uptake. The lowest uptake was observed with the β-cyclodextrin complex. The reverse phase HPLC analysis (column: Vydac C18, 250×4.6 mm, 5μ; mobile phase: methanol, 1 ml/min) of the cellular carotenoids indicated the simultaneous uptake of lutein and zeaxanthin from the complexes. The ratio between the two compounds was similar to the composition of the mixture used for complexation (1:1.6).

TABLE 4

A Comparison of the Uptake of Lutein and Zeaxanthin from Cyclodextrin
Complexes by Caco2 Cells

| Sample | Cellular Lutein + Zeaxanthin Uptake (Percent Increase) | |
|---|---|---|
| | 6-hr Incubation | 24-hr incubation |
| α-Cyclodextrin Complex | 16.1 | 35.2 |
| β-Cyclodextrin Complex | 18.1 | 28.7 |

TABLE 4-continued

A Comparison of the Uptake of Lutein and Zeaxanthin from Cyclodextrin
Complexes by Caco2 Cells

| Sample | Cellular Lutein + Zeaxanthin Uptake (Percent Increase) | |
| --- | --- | --- |
| | 6-hr Incubation | 24-hr incubation |
| γ-Cyclodextrin Complex | 16.1 | 39.9 |
| HP-β-Cyclodextrin Complex | 19.2 | 38.6 |

Example 5

Uptake of Lutein from Formulated
Lutein/γ-Cyclodextrin Complex In Vitro

The freeze-dried lutein/γ-cyclodextrin complex was formulated with medium chain triglycerides (MCT), polysorbate 80, and a combination of lecithin-soybean oil. The formulations were dispersed in PBS and treated with lipase to simulate the digestive process before incorporation into the culture medium.

As a comparison to the lecithin-oil formulation, free lutein incorporated into liposomes was used for the study. The concentration of lutein used and the testing conditions were similar to Example 1.

Observations

Figure 5:
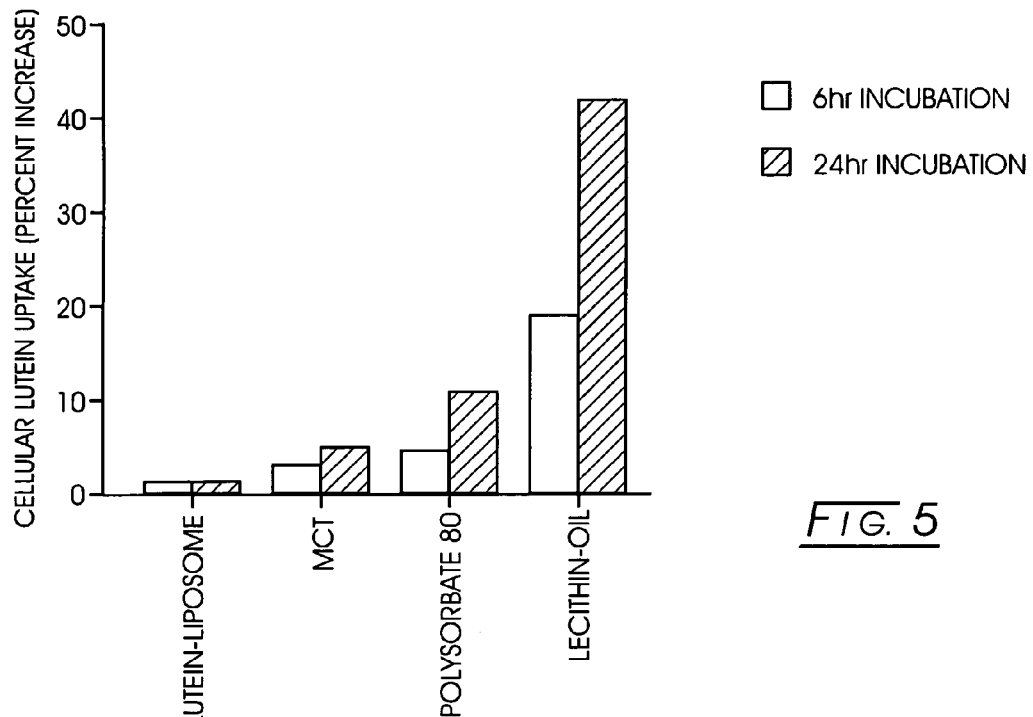
FIG. 5 represents the effects of formulating the complex on the uptake of lutein by Caco2 cells as reported in Example 5.

The results recorded are displayed below and in FIG. 5.

TABLE 5

Effect of Excipients on the Uptake of Lutein from the
Lutein-Cyclodextrin Complex by Caco2 Cells

| Formulation | Cellular Lutein Uptake (Percent Increase) | |
| --- | --- | --- |
| | 6-hr Incubation | 24-hr incubation |
| Free Lutein-Liposome | 1.2 | 1.2 |
| Lutein/cyclodextrin-Polysorbate 80 | 4.4 | 10.8 |
| Lutein/cyclodextrin-MCT- | 3.2 | 5.0 |
| Lutein/cyclodextrin-Lecithin-oil | 19.0 | 41.8 |

The above-tabulated results indicate that, of the three formulations tested, the lecithin-oil combination showed the highest uptake of lutein from the complex. The uptake also was significantly higher as compared to free lutein in liposomes. Both MCT and polysorbate 80 resulted in lower uptake from the complex.

Example 6

Human Study with Lecithin-Oil Formulation

A human study was conducted to compare the uptake of lutein from commercially available oil formulation (soft gelatin capsules) and the inventive lutein/γ-cyclodextrin complex in the lecithin-oil formulation (soft gelatin capsules). A single dose of 100 mg lutein was used for the study with nine volunteers.

Subjects

The subjects (30-65 years of age) were non-smokers, without any chronic diseases or gastrointestinal disturbances. The subjects were not taking any over-the-counter carotenoid supplements and were on their usual diets with modest amounts of carotenoids during the study.

Method

On the day of the study, 10 ml of blood was drawn to permit establishment of baseline values. After consumption of single doses of lutein from one of the formulations, blood samples were drawn at 24 hours. Serum was separated within 1 hr of blood draw and frozen immediately. After a two-week washout period, the study was repeated with the second formulation. The blood samples were drawn and processed as before.

Lutein and other carotenoids were extracted from the serum using Khachik's method (Khachik, F., Beecher, G. R., Goli, M. B., Lusby, W. R., and Daitch, C. E., "Separation and quantification of carotenoids in human plasma", *Methods in Enzymol.*, 213: 205-219, 1992). The lutein concentration was determined using reverse phase HPLC and diode array detection. The extraction method used sufficient serum for the detection of carotenoids by the diode array detector. The area under the curve was used for calculations. The data was analyzed using t test and $x^2$ test.

Observations

The results recorded are displayed below and in FIG. 6:

TABLE 6

A Comparison of Lutein Uptake In Vivo from the γ-Cyclodextrin Complex
in Lecithin-oil Formulation

| | Serum Lutein Percent Increase (Treated/Baseline) | |
| --- | --- | --- |
| Subject No. | Lutein-Oil | Lutein-Cyclodextrin/Lecithin-Oil |
| 1 | 1 | 40 |
| 2 | 17 | 108 |
| 3 | 20 | 64 |
| 4 | 25 | 96 |
| 5 | 37 | 63 |
| 6 | 54 | 90 |
| 7 | 73 | 73 |
| 8 | 179 | 188 |
| 9 | 204 | 236 |

Figure 6:
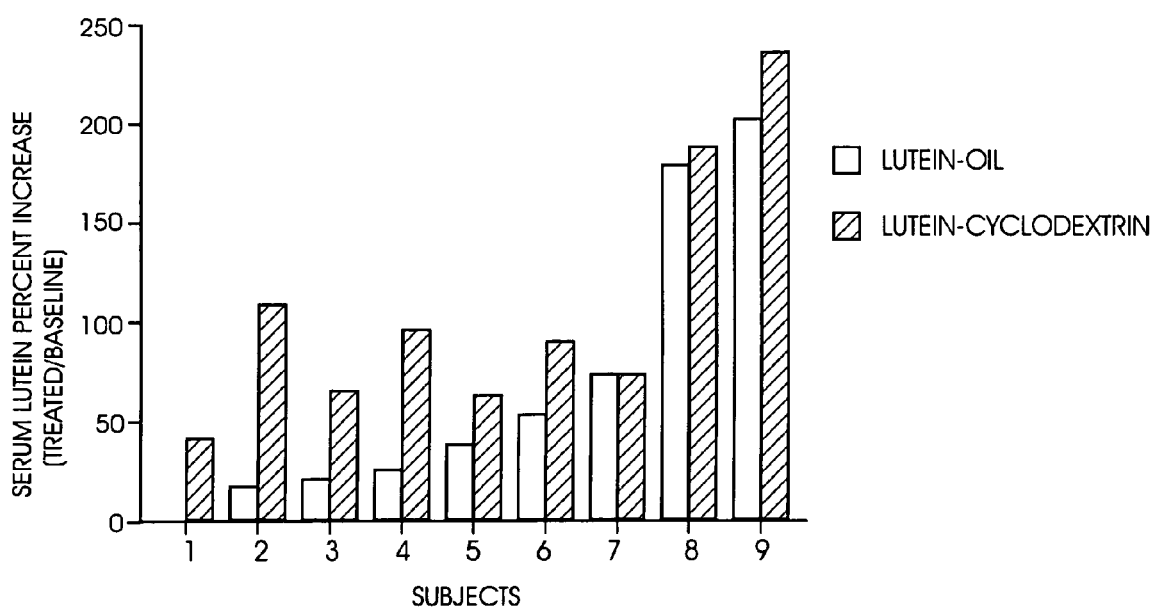
FIG. 6 represents a comparison of uptake of lutein from a lecithin-oil formulation in a human study as reported in Example 6.

Eight of the nine subjects had greater increase in lutein uptake over basal serum lutein (baseline) with the lutein-cyclodextrin complex formulation, as compared to the lutein delivered in oil as a soft-gel with the ninth subject having the same for both (FIG. 6). Measured against a baseline of 1.00, the mean increase in lutein uptake from the oil was 1.67, while the mean increase with lutein/cyclodextrin was 2.06. The mean difference between the oil and cyclodextrin increases was 0.39 or a 39% increase in uptake with the lutein-cyclodextrin complex (t test p<0.01).

Subjects with lower increases over baseline with lutein-oil showed higher increases with lutein-cyclodextrin over baseline. Conversely, subjects with higher increases of lutein-oil over baseline showed lower increases on lutein-cyclodextrin over baseline (FIG. 6). Comparing the four subjects lower in lutein oil uptake showed that they had a 60% improvement with the lutein-cyclodextrin, while the subjects with the higher uptake from lutein/oil showed a 20% improvement.

Example 7

Human Study with Vegetable Oil Formulation

The study was repeated with six subjects with the lutein/γ-cyclodextrin complex in vegetable oil formulation following a two-week washout period, using the protocol outlined in Example 6.

Observations

Figure 7:
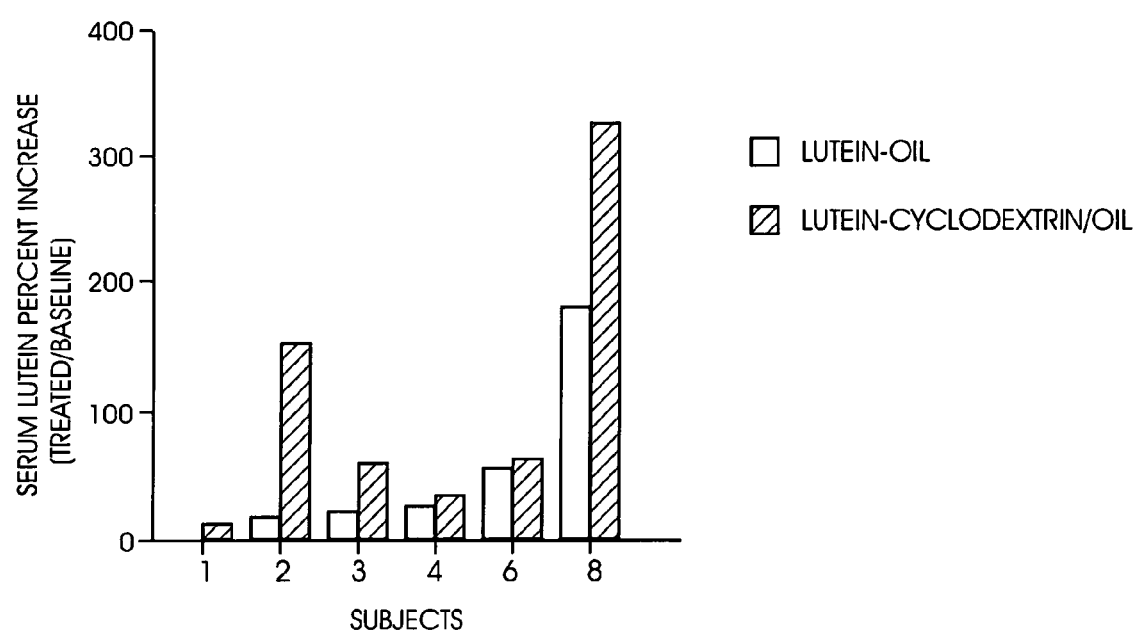
FIG. 7 represents a comparison of uptake of lutein from a vegetable oil formulation in a human study as reported in Example 7.

The results recorded are displayed below and presented in FIG. 7. Measured against a baseline of 1.00, the mean increase in lutein uptake from the oil was 1.49, while the mean increase with lutein/cyclodextrin was 2.15. The mean difference between the oil and cyclodextrin increases was 0.66 or a 66% increase in uptake with the lutein-cyclodextrin complex (t test $p<0.1$).

TABLE 7

A Comparison of Lutein Uptake In Vivo from the γ-Cyclodextrin Complex in Vegetable Oil Formulation

| Subject No. | Serum Lutein Percent Increase (Treated/Baseline) | |
|---|---|---|
| | Lutein-Oil | Lutein-Cyclodextrin/Oil |
| 1 | 1 | 11 |
| 2 | 17 | 151 |
| 3 | 20 | 57 |
| 4 | 25 | 33 |
| 6 | 54 | 61 |
| 8 | 179 | 326 |

We claim:

1. A bioavailable cyclodextrin/carotenoid complex having improved bioavailability compared to a spray-dried cyclodextrin/carotenoid complex, which comprises:
    a freeze-dried γ-cyclodextrin/lutein complex in a molar ratio of between about 0.5:1 and 10:1.

2. A method for improving the bioavailability of a cyclodextrin/carotenoid complex, for animal ingestion, the improvement which comprises the steps of:
    (a) forming a γ-cyclodextrin/lutein complex; and
    (b) freezing drying said γ-cyclodextrin/lutein complex to form a freeze-dried γ-cyclodextrin complex having improved bioavailability compared to a spray-dried γ-cyclodextrin/lutein complex.

3. The improved method of claim 2, wherein said γ-cyclodextrin/lutein complex is made for human ingestion.

* * * * *